United States Patent [19]
Chang et al.

[11] Patent Number: 4,470,814
[45] Date of Patent: Sep. 11, 1984

[54] METHOD OF ADHERING DENTURES

[75] Inventors: Tiang-Shing Chang, Westfield; Lucy J. Zientek, Bayonne; Arthur Viningauz, Sewaren, all of N.J.

[73] Assignee: Block Drug Company, Inc., Jersey City, N.J.

[21] Appl. No.: 528,849

[22] Filed: Sep. 2, 1983

Related U.S. Application Data

[63] Continuation-in-part of Ser. No. 333,019, Dec. 21, 1981, abandoned.

[51] Int. Cl.$^3$ ............................................. A61K 6/08
[52] U.S. Cl. ..................................... 433/168; 106/35; 433/180; 523/120
[58] Field of Search ............... 433/180, 168; 523/118, 523/120; 526/240; 525/361; 106/35

[56] References Cited

U.S. PATENT DOCUMENTS

| | | | |
|---|---|---|---|
| 2,798,053 | 7/1957 | Brown | 526/271 |
| 2,985,625 | 5/1961 | Jones | 526/271 |
| 3,058,958 | 10/1962 | Glavis | 526/240 |
| 4,267,103 | 5/1981 | Cohen | 526/240 |

Primary Examiner—Lorenzo B. Hayes
Attorney, Agent, or Firm—Ostrolenk, Faber, Gerb & Soffen

[57] ABSTRACT

A method for adhering dentures to oral mucosa with a denture fixative composition containing as the active fixative a partially neutralized and crosslinked polyacrylic acid or a precursor combination of the polyacrylic acid, neutralizing agent(s) and crosslinking agent(s) which is adapted to form the active fixative, and at least one hydrophilic polymer, preferably, sodium carboxymethyl cellulose, hydroxypropyl guar or sodium alginate.

10 Claims, No Drawings

METHOD OF ADHERING DENTURES

BACKGROUND OF THE INVENTION

This is a continuation-in-part of application Ser. No. 333,019, filed Dec. 21, 1981 now abandoned.

There are a number of desirable characteristics of a denture fixative composition. One extremely desirable attribute is that the fixative develops a high degree of tack upon contact with saliva in order that the dentures be held in place soon after they are seated in the mouth. Another highly desirable characteristic is that the denture fixative composition, upon contact with saliva, forms a viscous mucilage of high cohesive strength which can spread over the denture-mucosa interface and form a thin, uniform, and continuous film to fill the gaps which naturally occur between the surfaces of the oral mucosa and that of the prosthesis with which they are in contact.

Numerous pharmaceutical formulations have employed polyacrylic acid. The use of such polyacrlic resins has, in the past, been primarily directed toward the exploitation of their thickening, suspending and emulsifying capabilities when the polymer is partially or wholly neutralized in amide or hydroxy solvents with an inorganic base, water soluble amine or some other combination thereof (see, e.g., B. F. Goodrich Service Bulletin, GC-67).

In aqueous systems, the partially or wholly neutralized polyacrlic acid generates a gel which has low cohesive strength with a structure that may be easily ruptured when it is subjected to stresses such as those that occur during mastication.

The cohesive strength of polyacrylic acid gels can be controlled by partial neutralization and partial crosslinking of the resin and the resulting partly crosslinked and neutralized polyacrylic acid derivatives have been found to provide excellent fixative properties for prolonged periods of time when combined with certain hydrophilic polymers.

It is accordingly the object of this invention to provide new dental fixative compositions which exhibit sufficient cohesive strength to resist stresses such as those that occur upon mastication and which retain their fixative properties for prolonged periods of time. This and other objects of the invention will become apparent to those skilled in this art from the following detailed description.

SUMMARY OF THE INVENTION

This invention relates to denture fixative compositions and more particularly to such compositions in powder, liquid or cream form which combine a partially neutralized and crosslinked polyacrylic acid with at least one hydrophilic polymer. The polyacrylic acid can be neutralized and crosslinked in situ, or partially neutralized prior to incorporation into the composition and then crosslinked in situ, or may be partially neutralized and crosslinked prior to incorporation into the denture fixative composition or may be partially crosslinked prior to incorporation into the composition and then neutralized in situ. The neutralizing agent can be a salt, base or oxide of a monovalent cation such as an alkali metal ion and the crosslinking agent can be a salt, base or oxide of a divalent cation and/or a polyhydroxy compound. The hydrophilic polymer can be either synthetic gum such as a cellulose derivative, polyethylene oxide, or natural gum such as xanthan gum, guar, alginates and karaya.

DESCRIPTION OF THE INVENTION

The present invention provides denture fixative compositions in powder, liquid and cream forms which, when in contact with saliva, develop a high degree of tack and uniform viscous mucilages of high cohesive strength which when spread over the denture-mucosa interface, provide superior denture stabilizing properties. The active fixatives are certain derivatives of polyacrylic acid which, in the form of a 1% aqueous solution, exhibit a pH of at least 4.5 and preferably about 5.0 to 7.0. The polyacrylic acid derivatives are prepared by the neutralization and crosslinking of at least 10% up to about 90% of the total number of initial carboxyl groups in the polyacrylic acid.

The polyacrylic acid used in the present invention is also known as carboxypolymethylene or carboxyvinyl polymer and has a repeating unit of the formula

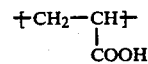

Such polyacrylic acids have molecular weights of about 500,000 to about 5,000,000, preferably about 2,000,000 to 4,000,000 and most preferably about 3,000,000.

The crosslinking agents employed are the dentally acceptable salts, oxides and bases of divalent cations and/or polyhydroxy compounds. The preferred divalent cations are alkaline earth metal cations and most preferably magnesium and calcium, although other divalent cations can also be employed. Typical polyhydroxy compounds include glycerin, propylene glycol, ethylene glycol, tetramethylene glycol, and the like, and generally have 2 to about 6 carbon atoms and preferably 2 or 3 hydroxy groups. The preferred polyhydroxy compounds are glycerin and propylene glycol.

The neutralizing agents which can be employed in the present invention are the dentally acceptable salts, oxides and bases of monovalent cations. Such cations are preferably alkali metal cations and most preferably sodium and potassium cations, although other monovalent cations can also be used. The anions of the salts and bases can be such diverse materials as hydroxide, acetate, lactate, gluconate, carbonate, and the like. It will be appreciated that any neutralization or crosslinking agent which is used must be dentally acceptable and any material which forms toxic or irritating by-products should be avoided.

The neutralizing agents and crosslinking agents are employed in an amount sufficient to neutralize and crosslink about 20-90% of the total number of initial carboxy groups in the polyacrylic acid. The crosslinking agents are incorporated in sufficient quantity to crosslink about 10-80% of the total initial carboxy groups and the neutralizing agent in an amount sufficient to neutralize about 10-70% of the initial carboxyl groups. The crosslinking agents are preferably used in an amount sufficient to crosslink about 15-65% of the total initial carboxyl groups and the neutralizing agent in an amount sufficient to neutralize about 10-50% when the crosslinking agent is a divalent salt and about 20-60% when the crosslinking agent is a polyhydroxyl compound.

The relative proportions of divalent to monovalent cations, as well as the quantity of polyhydroxy compound to be incorporated with the polyacrylic acid are major factors affecting the characteristics of the resulting reaction product such as its degree of water sensitivity and solubility, its water absorption capacity and its rates of hydration and dissolution, as well as other properties such as the cohesive and adhesive strength of the gels formed during hydration of the derivative. Relatively small changes in proportions can have a significant effect on the performance profile of the polyacrylic acid derivative as a denture fixative. Moreover, the characteristics of the derivative which are the result of the neutralization reaction with the monovalent cation can further be modified by the appropriate selection of the particular salt, oxide or base chosen to serve as a neutralizing agent. Appropriate optimization to achieve a desired balance of properties in accordance with the parameters described above is well within the skill of those working within this art. However, it is presently preferred that the divalent to monovalent cation mole ratio be in the range of about 1:4 to 4:1, most preferably about 1:2.5 to 2.5:1, and that the polyhydroxy compound be employed in quantities sufficient to react with up to about 30% of the total initial carboxy groups in the polymer and most preferably less than about 20%. Of course, various mixtures of neutralizing agents and crosslinking agents can be employed.

A particularly convenient embodiment of the present invention is to prepare a denture fixative composition which contains the partially neutralized salt of polyacrylic acid together with the intended crosslinking agent and permitting the crosslinking reaction to occur in situ with the adhesive exposed to saliva. Alternatively, the composition can contain the partially crosslinked polyacrylic acid with the intended neutralizing agent but in this instance, more neutralizing agent should be employed than in the embodiment just mentioned. In another alternative, appropriate neutralizing and crosslinking agents can be incorporated with polyacrylic acid in anhydrous formulations. In this case, the corresponding reactions will occur spontaneously in the presence of water making the system particularly suitable for use in denture adhesive or fixative compositions. It will be appreciated that such compositions are generally formulated incorporating an anhydrous vehicle such as petrolatum and mineral oil in cream formulation in order to protect their water-activated ingredients from premature contact with moisture. In such formulations, additionally, it is judicious to avoid the use of neutralizing and crosslinking agents which generate a pH higher than about 10 immediately after the formulation comes into contact with saliva and thereby increase the risk of irritation and/or injury to the oral mucosa.

The suitable hydrophilic polymers used in the invention can be synthetic gums such as cellulose derivatives, polyethylene oxide or natural gums such as guar, alginate, karaya and xanthan gum, preferably, sodium carboxymethyl cellulose, hydroxypropyl guar and sodium alginate. The further improvement of the adhesive property apparently is due to a synergistic effect brought about by the combination.

The denture fixative combination of the polyacrylic acid derivatives and hydrophilic polymer is incorporated into the denture fixative composition in an effective fixative amount. The amount will vary considerably, depending on the particular polyacrylic acid derivatives, the degree of neutralization and crosslinking, and the amount of the hydrophilic polymer. In general, the fixative is about 10–70 weight percent or more of the denture fixative composition, and preferably about 15–50 weight percent, depending on the particular modified polyacrylic acid resin, particular hydrophilic polymer and the other ingredients in the composition. All of such other excipients, ingredients and carriers should be, of course, dentally acceptable. In general, the polyacrylic acid derivative will constitute about 10–80% of the fixative mixture and preferably about 30–70 weight percent.

Among the other ingredients which are used in the denture fixative compositions, all of which come under the heading of a dentally (orally) acceptable excipient there can be mentioned flavoring agents, coloring agents, preservatives, thickeners and vehicles such as petrolatum, mineral oil and the like in cream type formulations, and non-toxic anti-caking agents such as silica, magnesium stearate, talc, dicalcium phosphate anhydrous and the like can be present.

In order to further illustrate the invention, various examples are set forth below. In these examples, as throughout this specification and claims, all parts and percentages are by weight and all temperatures are in degrees Celsius unless otherwise indicated.

EXAMPLE 1

27 parts of sodium hydroxide were dissolved in a solution which contained 10 parts glycerin and 819 parts water in a suitable vessel. 145 parts of a polyacrylic acid, sold under the trademark Carbopol 934P, molecular weight approximately 3,000,000, were slowly added to the rapidly agitated solution. The resulting product was dried and ground through a 100 mesh sieve (U.S. Standard Sieve Series) to realize a powder which had a packed bulk density of about 0.8 g/ml and which had a pH of a 1% aqueous solution of 5.4.

The partially neutralized and crosslinked polyacrylic acid was incorporated into the following denture adhesive composition:

Sodium/glycerin polyacrylic acid, pH 5.4: 25 parts
Xanthan gum: 10 parts
Mineral oil and petrolatum base: 64 parts
Flavor, color, preservative: 1 part

EXAMPLE 2

Sodium hydroxide (53 parts) and calcium hydroxide (146 parts) were added to 1700 parts of a 70% methanol aqueous solution. To the resulting slurry, 460 parts of a polyacrylic acid having a molecular weight of about 1,200,000 were added slowly with vigorous agitation. After filtration and drying under vacuum, the resulting product was ground and screened through a 100 mesh sieve. The pH of 1% aqueous solution of the partially neutralized and crosslinked polyacrylic acid was 5.6.

The modified acrylic acid was then incorporated into a denture fixative composition of the present invention as follows:

Ca/Na polyacrylic acid: 30 parts
Sodium carboxymethylcellulose: 10 parts
Petrolatum: 44 parts
Mineral Oil: 15 parts
Flavor, color, preservative: 1 part

EXAMPLE 3

To 92 parts of a 70% methanol aqueous solution were added 40 parts of KOH and 40 parts of MgO. The slurry which resulted was vigorously agitated and 250 parts of a polyacrylic acid having an average molecular weight of 3,000,000 added. The product was filtered, dried, and ground through a 100 mesh sieve, and was found to have a packed bulk density of approximately 0.7 g/ml. The pH of a 1% aqueous solution was 5.8. The partially neutralized and crosslinked polyacrylic acid was then incorporated into the following liquid denture adhesive formulation:

K/Mg polyacrylic acid: 25 parts
Methylcellulose: 10 parts
Mineral oil: 64 parts
Flavor and preservative: 1 part

EXAMPLE 4

A solution containing 28 parts sodium hydroxide, 890 parts water and 11 parts glycerin was reacted with 74 parts of a polyacrylic acid resin having a molecular weight of about 4,000,000. The resulting product was filtered and dried under vacuum and then milled to a fine powder which had a packed bulk density of 0.8 g/ml. The pH of a 1% aqueous solution of this modified polyacrylic acid was 6.6 and it was incorporated into the following denture adhesive formulation:

Na/glycerin polyacrylic acid: 38 parts
Methylcellulose: 7 parts
Mineral oil and petrolatum: 54 parts
Flavor, color, preservative: 1 part The following examples illustrate denture fixative compositions containing the partially neutralized derivative of polyacrylic acid which are formed so that the crosslinking reaction occurs in situ upon exposure of the adhesive to saliva.

EXAMPLE 5

A partially neutralized salt of polyacrylic acid was obtained by reacting 100 parts of polyacrylic acid of about 3,000,000 average molecular weight with a mixture containing 10.8 parts glycerin and 790 parts of a 0.2M sodium hydroxide solution. After filtration and drying, the product was ground. The pH of a 1% aqueous solution of the resulting polyacrylic acid was 4.5.

The partially neutralized polyacrylic acid is incorporated in a cream base with a sufficient quantity of magnesium oxide to provide a divalent/monovalent cation ratio of approximately 2.3:1 in the following denture fixative composition:

Na/glycerin polyacrylic acid: 24 parts
MgO, U.S.P.: 3 parts
Polyethylene oxide (4,000,000 average molecular weight): 9 parts
Petrolatum and mineral oil: 63 parts
Flavor, preservative and color: 1 part

EXAMPLE 6

200 parts of a polyacrylic acid having an average molecular weight of about 3,000,000 were slowly added to a solution containing 40 parts of sodium hydroxide in 870 parts of a 70% aqueous methanol solution and the resulting precipitate filtered and dried. After grinding, the powder is incorporated with a polyhydroxy crosslinking compound in liquid denture adhesive in the following proportions:

Na/polyacrylic acid: 10.0 parts
Sodium carboxymethylcellulose: 15.0 parts
Propylene glycol: 1.5 parts
Mineral oil: 72.5 parts
Flavor, preservative, color: 1.0 part

EXAMPLE 7

A partially neutralized sodium salt of polyacrylic acid with a pH of 4.5 is incorporated with calcium hydroxide in a cream denture fixative composition as follows:

Na alginate: 5.0 parts
Na polyacrylic acid: 30.0 parts
Calcium hydroxide: 8.0 parts
Petrolatum and mineral oil: 56.2 parts
Flavor, preservative and color: Q.S.

EXAMPLE 8

The partially neutralized polyacrylic acid of Example 7 is incorporated with magnesium oxide as the crosslinking agent in the following denture adhesive cream:

Xanthan gum: 10.0 parts
Na polyacrylic acid: 30.0 parts
MgO: 5.0 parts
Petrolatum and mineral oil: 53.8 parts
Flavor, preservative and color: 1.2 parts The following examples illustrate formulations in which the polyacrylic acid, neutralizing agent and crosslinking agents are incorporated in an anhydrous formulation.

EXAMPLE 9

The ingredients listed below were compounded to form a denture fixative composition with superior stabilizing properties:

Polyacrylic acid resin, average molecular weight 4,000,000: 20.0 parts
Xanthan gum: 15.0 parts
Sodium phosphate, tribasic: 5.0 parts
Magnesium oxide (MgO): 3.0 parts
Petrolatum and mineral oil: 57.0 parts

EXAMPLE 10

The following components were blended to form a liquid denture adhesive:

Polyacrylic acid resin, average molecular weight 3,000,000: 16.0 parts
Calcium hydroxide: 2.5 parts
Sodium phosphate, tribasic: 3.5 parts
Na carboxymethylcellulose: 14.0 parts
Mineral oil: 63.0 parts
Flavors, preservative, color: 1.0 part

EXAMPLE 11

The ingredients listed below are compounded in a denture fixative cream:

Polyacrylic acid resin, average molecular weight 3,000,000: 23.5 parts
Potassium phosphate, tribasic: 6.5 parts
Magnesium oxide: 3.5 parts
Methylcellulose: 5.0 parts
Glycerol: 1.5 parts
Mineral oil and petrolatum: 59.3 parts
Flavors, preservative, color: 0.7 part

EXAMPLE 12

The following materials are blended and introduced into 49 parts of a petrolatum and mineral oil base to form a cream denture fixative composition:

Polyacrylic acid resin, average molecular weight 7,500,000: 30.0 parts
Hydroxypropyl guar: 5.0 parts
Potassium phosphate, tribasic: 7.1 parts
Magnesium oxide: 6.0 parts Flavors, preservative, color: 1.6 parts After addition of the powder components to the base, 1.5 parts of propylene glycol are blended in to act as a polyhydroxy crosslinking compound. The result is a smooth homogeneous cream of superior denture stabilizing properties when hydrated by saliva.

EXAMPLE 13

400 parts of polyacrylic acid having a molecular weight of about 3,000,000 were dissolved in 1,700 parts of water. To the resulting solution, 74 parts of calcium hydroxide were added slowly with vigorous agitation. The resulting product was dried and ground through a 100 mesh sieve. The pH of a 1% aqeuous solution of the partially crosslinked polyacrylic acid was about 5.2.

The partially crosslinked polyacrylic acid was incorporated into the following denture adhesive composition:

Calcium polyacrylic acid: 35.0 parts
Sodium phosphate, tribasic: 10.0 parts
Hydroxypropyl guar gum: 20.0 parts
Dicalcium phosphate anhydrous: 34.5 parts
Flavor, preservative: 0.5 part It will be appreciated from the foregoing that the derivatives of polyacrylic acid in combination with at least one hydrophilic polymer upon hydration yield gels of high tack and great cohesive strength and are therefore capable of imparting improved stabilization characteristics to the denture fixative compositions in which they are incorporated. The invention provides the advantage that those properties of the denture adhesive formulations such as adhesive and cohesive strength, hydration and dissolution rates and water absorption capacities, can be varied within a broad range by controlling the balance between the neutralization and crosslinking in the polyacrylic acid resins as well as by the selection of the particular compounds used as such agents. A particular advantage of the invention is that the crosslinking and neutralization reactions can occur at close to body temperature in an aqueous environment and, as a sult, may be generated in situ by exposure of the appropriate agents to the polyacrylic acid resin in saliva.

The various embodiments of the invention which have been described and disclosed herein were set forth in order to further illustrate the invention but were not intended to limit it. Various changes and modifications can be made without departing from the spirit and scope of the invention.

What is claimed is:

1. In a method of adhering dentures to oral mucosa employing a denture fixative which spreads over the denture-mucosa interface to fill the gaps therebetween, the improvement which comprises employing, as the denture fixative, a composition comprising a dentally acceptable excipient and an effective denture fixative amount of a combination of (a) polyacrylic acid which has been partially neutralized by at least one monovalent cation and partially neutralized by at least one monovalent cation and partially crosslinked by at least one agent selected from the group consisting of the salts, bases and oxides of divalent cations and polyhydroxy compounds such that 20-90% of the initial carboxyl groups have been neutralized or crosslinked, wherein a 1% aqueous solution of said partially neutralized and crosslinked polyacrylic acid has a pH of at least about 4.5, or a precursor combination of polyacrylic acid, neutralizing agent and crosslinking agent or of partially neutralized polyacrylic acid and crosslinking agent or of partially crosslinked polyacrylic acid and neutralizing agent, said precursor combination adapted to form said partially neutralized and crosslinked polyacrylic acid in an aqueous environment, and (b) at least one hydrophilic polymer.

2. The method of adhering dentures of claim 1 wherein said polyacrylic acid has an average molecular weight of about 2,000,000-4,000,000, said monovalent cation is sodium or potassium, said divalent cation is magnesium or calcium and said polyhydroxy compound is glycerin or propylene glycol.

3. The method of adhering dentures of claim 2 where the amount of neutralizing agent is sufficient to neutralize about 10-70% of the initial carboxyl groups and the amount of crosslinking agent is sufficient to crosslink about 10-80% of the initial carboxyl groups.

4. The method of adhering dentures of claim 3 wherein a 1% aqueous solution of said partially neutralized and crosslinked polyacrylic acid has a pH of about 5.0-7.0.

5. The method of adhering dentures of claim 4 wherein said fixative is said precursor combination.

6. The method of adhering dentures of claim 5 wherein the precursor combination comprises partially neutralized polyacrylic acid and crosslinking agent.

7. The method of adhering dentures of claim 1 wherein said polyacrylic acid has an average molecular weight of about 500,000-5,000,000, said divalent cation is an alkaline earth metal cation, said polyhydroxy compound has 2 to 6 carbon atoms and said monovalent cation is an alkali metal cation, and wherein said hydrophilic polymer is a natural or synthetic gum.

8. The method of adhering dentures of claim 3 wherein the ratio of monovalent cation to divalent cation is about 1:4-4:1 and the amount of polyhydroxy compound is sufficient to react with up to 30% of the initial carboxyl groups.

9. The method of adhering dentures of claim 3 wherein said fixative is about 10-70 wt.% of said composition.

10. The method of adhering dentures of claim 7 wherein said hydrophilic polymer is carboxymethyl cellulose, hydroxpropyl guar or sodium alginate.

* * * * *